(12) United States Patent
Peter et al.

(10) Patent No.: US 8,343,099 B2
(45) Date of Patent: Jan. 1, 2013

(54) DEVICE FOR METERED ADMINISTRATION OF A LIQUID PRODUCT

(75) Inventors: Daniel Peter, Niederwangen (CH); Beat Spoerri, Bibern (CH)

(73) Assignee: Roche Diagnostics International AG, Rotkreuz (CH)

( * ) Notice: Subject to any disclaimer, the term of this patent is extended or adjusted under 35 U.S.C. 154(b) by 1445 days.

(21) Appl. No.: 11/388,216

(22) Filed: Mar. 23, 2006

(65) Prior Publication Data
US 2007/0017512 A1    Jan. 25, 2007

(30) Foreign Application Priority Data
Mar. 24, 2005    (EP) .................................. 05006544

(51) Int. Cl.
*A61M 37/00* (2006.01)
(52) U.S. Cl. ......................... 604/131; 604/154
(58) Field of Classification Search .............. 604/131, 604/154; 128/DIG. 1
See application file for complete search history.

(56) References Cited

U.S. PATENT DOCUMENTS

| | | | |
|---|---|---|---|
| 5,106,375 A | 4/1992 | Conero | |
| 5,492,534 A | 2/1996 | Athayde et al. | |
| 5,501,665 A * | 3/1996 | Jhuboo et al. | 604/65 |
| 5,582,591 A | 12/1996 | Cheikh | |
| 5,616,123 A | 4/1997 | Cheikh | |
| 6,368,314 B1 | 4/2002 | Kipfer et al. | |
| 6,613,023 B2 | 9/2003 | Kirchhofer et al. | |
| 6,620,137 B2 | 9/2003 | Kirchhofer et al. | |
| 6,659,980 B2 * | 12/2003 | Moberg et al. | 604/154 |
| 2002/0087147 A1 * | 7/2002 | Hooper et al. | 604/892.1 |
| 2003/0073954 A1 | 4/2003 | Moberg et al. | |
| 2004/0122366 A1 | 6/2004 | Kazemzadeh | |

FOREIGN PATENT DOCUMENTS

| | | |
|---|---|---|
| DE | 41 33 402 C1 | 1/1993 |
| DE | 197 17 107 A1 | 11/1998 |
| WO | WO 01/72357 A2 | 10/2001 |
| WO | WO 2004/089448 A1 | 10/2004 |

* cited by examiner

*Primary Examiner* — Kevin Sirmons
*Assistant Examiner* — Deanna K Hall
(74) *Attorney, Agent, or Firm* — Dinsmore & Shohl, LLP

(57) ABSTRACT

A device for metered administration of a liquid product including a container for the product, a delivery mechanism which acts on the product located in the container and delivers product from the container by means of an axial output movement in a delivery direction, and an inherently axially rigid housing support structure which supports the container in and counter to the delivery direction, wherein the housing support structure has, over the axial length of the container, an axial thermal expansion coefficient which, within a temperature range in which the device is used, corresponds at least substantially to the axial thermal expansion coefficient of the container.

29 Claims, 7 Drawing Sheets

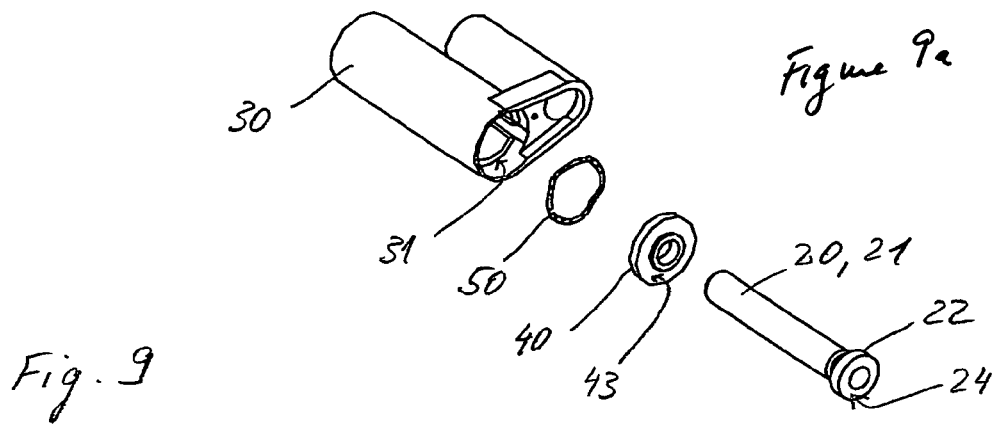
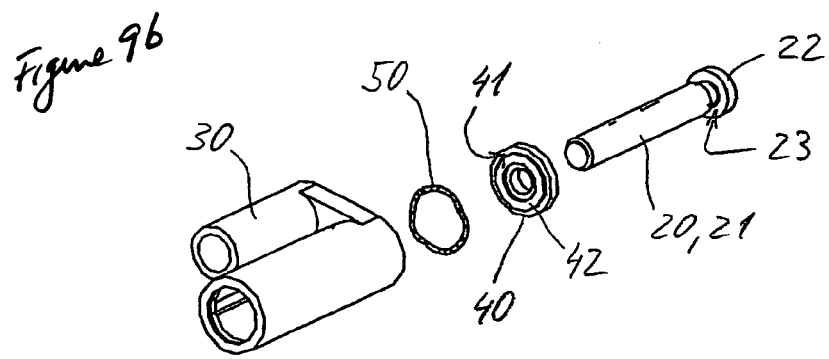
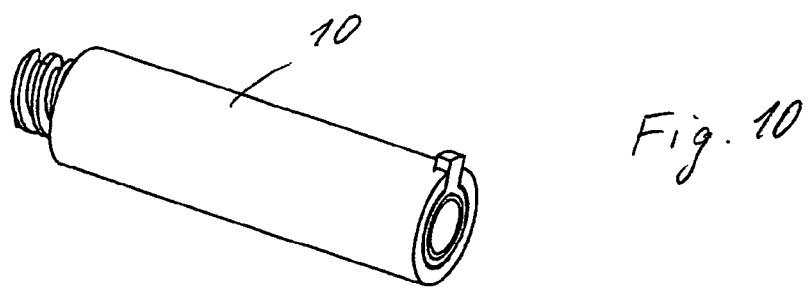

DEVICE FOR METERED ADMINISTRATION OF A LIQUID PRODUCT

CROSS-REFERENCE TO RELATED APPLICATION

This application claims the benefit of German Application No. 05006544.0, filed Mar. 24, 2005, the content of which is incorporated in its entirety herein by reference.

BACKGROUND

The present invention relates to devices and methods for delivering, administering or dispensing substances, and to methods of making and using such devices. More particularly, it relates to devices and methods for metered administration of liquid products in biotechnology applications, preferably in medical applications, including veterinary and pharmaceutical applications. It relates in particular to infusion and injection appliances and devices, and methods of making and using such appliances and devices.

In various treatments, great importance is attached to the accuracy of the metering of products to be administered, for example in the administration of insulin in the treatment of diabetes. Infusion appliances and injection appliances are common in which a product to be administered is dispensed from a product reservoir by means of a motor-driven reciprocating piston pump in the case of infusion appliances or by means of a manually activated reciprocating piston pump in the case of injection appliances. In infusion appliances, the reciprocating piston is usually driven by a rotary drive mechanism, the rotation movement of the drive mechanism being converted by means of a spindle drive into the linear movement of the piston. In injection appliances, a spindle drive is often used for selecting the product dose to be administered, while the linear movement of the piston is effected directly by hand. In injection appliances, rack-and-pinion gears are also customary. A common feature of the above examples of appliances used for administration is that the accuracy of the metering depends critically on the degree of precision with which it is possible to predetermine the distance that the piston has to travel to deliver a defined dose of product.

Infusion appliances and injection appliances of the type mentioned above are described by DE 198 40 992 A, DE 198 22 031 C and DE 199 00 827 C, for example.

Particular demands on metering accuracy and precision have to be met by infusion appliances with which the product is often dispensed, delivered or administered over fairly long periods of time in small and discrete boluses or doses. Structural features serving in principle to improve the accuracy of the metering may at the same time also have a disruptive effect on, for example, the capacity for occlusion detection. An infusion appliance with advantageously configured, automatic occlusion detection is described in DE 198 40 992, to which reference is hereby made for the purposes of the present invention. A further appliance with occlusion detection is described in WO 01/72357 A2. For the occlusion detection, the entire delivery means is supported on the housing of the infusion appliance via a sensor. To ensure that this manner of support does not permit relative movements between the delivery means and the product container, WO 01/72357 A2 proposes, for assembly of the appliance, that the entire delivery means is first pressed in the delivery direction of the piston as far as an abutment formed by the housing, that the delivery means is then essentially relieved of the pressure, and finally that a closure cap is fitted into a rear opening of the housing and is adhesively bonded to the housing. The cap is intended to hold the delivery means in abutment against the housing. As an alternative configuration, it is also proposed that the delivery means, at its end remote from the piston, is supported on the rear base of the housing by means of an elastic sealing ring, and that a hollow space remaining between the rear face of the delivery means and the base of the housing is filled with a filler material, for example with silicone. The filler material should be substantially non-compressible, so as not to relieve the load on the sensor.

SUMMARY

It is an object of the invention to deliver the desired dose of product more accurately than before possible with devices for metered administration of liquid products.

In one embodiment, the present invention comprises a device for administering a dose of a substance comprising a container having an axial length and an axial thermal expansion coefficient, a delivery mechanism, and a support structure which supports the container, wherein the support structure has, over the axial length of the container, an axial thermal expansion coefficient which, within a temperature range in which the device is used, corresponds at least substantially to the axial thermal expansion coefficient of the container.

In one embodiment, the present invention comprises a device for metered administration of a liquid product including a container for the product, a delivery mechanism which acts on the product located in the container and delivers product from the container by means of an axial output movement in a delivery direction, and an inherently axially rigid housing support structure which supports the container in and counter to the delivery direction, wherein the housing support structure has, over the axial length of the container, an axial thermal expansion which, within a temperature range in which the device is used, corresponds at least substantially to the axial thermal expansion of the container.

A device for metered administration of a liquid product, in accordance with one embodiment of the present invention, comprises a housing, a reservoir for the product, and a delivery means. The housing itself can form the reservoir directly. In some preferred embodiments, however, a container, for example an ampoule or the like, forms the reservoir. The container is held by the housing in a defined position. Such a container may be inserted into the housing. As is customary in the case of ampoules, the container can be prefabricated by being filled with a defined quantity of a product or substance to be delivered and sealed by a piston that seals the rear of the container, the piston already being received in said container. Prefabricated ampoules of this kind are customary for self-administration of insulin in the treatment of diabetes. The product can be the aforementioned insulin, a growth hormone, and, in principle, any other medically active or, for example, cosmetically active product. A device according to the present invention may preferably be designed for self-administration.

The delivery means comprises at least one drive member and at least one output member. The drive member is preferably driven by motor, if the device is an infusion appliance, and preferably by hand, if the device is an injection appliance, such that it executes a drive movement. The drive member and the output member are mechanically coupled to one another in such a way that the drive movement of the drive member effects an output movement of the output member. The output movement is or comprises an axial movement which, in some embodiments, is preferably supported axially by the housing via the drive member. The axial movement can be superposed by another movement or by several other movements. However, in some embodiments, the output movement is preferably a purely linear axial movement.

In some embodiments, the housing can be formed in several parts, in particular in two parts, with a first housing structure which preferably forms a housing shell structure, in one embodiment, an at least substantially closed outer shell of the housing. The first housing structure may be made from plastic, for example by injection moulding, i.e., in a conventional manner in terms of the material and also in terms of the shaping operation. The multi-part housing also comprises a second housing structure that axially supports the container and preferably also the delivery means, or at least those components of the delivery means whose axial thermal expansion critically influences the metering accuracy.

Because of its function, the second housing structure may be referred to herein as the housing support structure or simply just as the support structure. Although, in some embodiments, the housing preferably comprises a shell structure in addition to the support structure, it is also possible, in alternative configurations of the housing, for the support structure itself to form the latter above.

Both in the design of the housing with shell structure and in the design without shell structure, the support structure is inherently axially rigid. This can be achieved by the support structure being in one piece along the axial length of the container to be supported. If, as is preferred in some embodiments the support structure supports other components, the axial rigidity can be achieved by its being in one piece along a correspondingly greater axial length. However, the support structure can itself be formed from a plurality of inherently axially rigid support structure parts which are connected to one another in an axially rigid manner, such that the support structure resulting from the plurality of parts is overall once again inherently axially rigid at least along the axial length between its at least two support locations.

According to the present invention, the support structure supports the container in and counter to the delivery direction. The support structure has, over the length of the container, an axial thermal expansion which, within a temperature range in which the device is used, corresponds at least substantially to the axial thermal expansion of the container. If, as is preferred in some embodiments, the container is supported directly, i.e., without intermediate components, in and counter to the delivery direction on the support structure, the axial thermal expansions that are to be compared are measured for the axial section of the support structure which supports the container in and counter to the delivery direction, and for the axial section of the container which extends between the axial support locations of the container. For the comparison, the axial lengths are measured at a temperature from the range of temperatures within which the device is used. The range of temperatures of use covers temperatures from about −20° C. to +40° C.

In conventional administering devices, the container, which is usually made of glass, is supported in and counter to the delivery direction on a plastic housing. The coefficients of thermal expansion of the customary plastic materials differ from the coefficients of thermal expansion of the customary glass materials by approximately a factor of 10, i.e., by an order of magnitude. The axial thermal expansions of the housings and product containers of conventional administering devices also differ accordingly. Against this background, an axial thermal expansion of the support structure measured in [m] is, within the meaning of the invention, also still considered as being substantially identical to the axial thermal expansion of the container if the two axial thermal expansions under discussion in the invention differ by not more than about 500%. More preferably, the axial thermal expansions do not differ by more than about 300%. The support structure should be made from a material having a coefficient of axial thermal expansion that differs by not more than about 500% from the coefficient of thermal expansion of the material of the container. If the support structure is not produced homogeneously from one material for which there is a single coefficient of thermal expansion, then the above statements are intended to apply for all the materials processed in the support structure.

The container can, in some embodiments, be made of glass, as is customary or usual.

In some embodiments, the support structure is ideally made from the same material as the container, but this will scarcely be possible when a glass container is used. Another preferred material candidate is a metal support structure that satisfies the conditions according to the invention in respect of axial thermal expansion. A further option is to form the support structure as a composite body, for example with a support matrix which satisfies the conditions according to the invention in respect of its axial thermal expansions, and with a plastic material with which the support matrix is encapsulated and in which the support matrix is anchored. A suitable composite body can also be formed as a fibre-reinforced plastic body, with axially extending fibres, for example metal fibres, embedded in its plastic matrix. Suitable materials other than metal or plastic may be used.

If the housing is made in several parts with a shell structure and support structure, in some embodiments, the support structure is preferably connected to the shell structure with a form fit, or with a form fit and force fit, and can in particular be inserted into the shell structure. If the shell structure is a cast part, the support structure can, for example, also be encapsulated by the material of the shell structure. A cohesive connection between the shell structure and the support structure is also possible.

Not only if, but in particular if, the support structure is formed as a composite body for achieving the thermal expansion behaviour according to the present invention, it is possible to do without an additional housing structure such as, for example, the shell structure into which the support structure is inserted. Shell structure and support structure merge together in such a case. In this connection, it is not necessary for the whole of the combined shell and support structure to have the thermal expansion behaviour according to the present invention in a uniform manner. It suffices for the thermal expansion behaviour according to the present invention to be provided in axial sections, for example by embedding fibre material only within a certain axial section.

An advantage of the support structure according to the present invention is that the container does not have to be axially supported on the housing by means of a compensating spring, but instead can be axially fixed by means of axial abutments at either end. When the variations in axial length are compensated by means of a compensating spring, the axial position of the container in relation to the delivery means changes. However, the change in position detracts from the metering accuracy of the delivery. For the axial supporting action in and counter to the delivery direction, the container is therefore preferably in abutment against the support structure both in and also counter to the delivery direction, such that it is axially fixed relative to the support structure. If, despite the support structure according to the invention, the container is supported on the support structure by means of a compensating spring, at least the variations in the axial lengths of container and support structure are much smaller than the variations in the conventional administering devices, so that in this case too the metering accuracy of the delivery is improved compared to the conventional administering devices if a compensating spring is used. The compensating spring excursions are then shorter in some embodiments, an axially rigid supporting action between abutments is preferred, however. For the supporting action, the support structure can form a support shoulder directly for the container both in the delivery direction and counter to the delivery direction. In or counter to the delivery direction, or in principle also in both directions, the supporting action can however also be realized indirectly, i.e. via one or more further components, for example the delivery means, in which case the further component in question, for example the delivery means, or the possible further components are axially supported on the support structure, in the manner described above, in order to support the container in a manner involving minimal play. In an indirect supporting action of this kind, it is may be preferable for the components in question to be rigidly supported on one another in the axial direction, i.e., abutting one another. However, the above comments regarding a possible spring element arranged between two components also apply here.

Of the support shoulders required for the axial supporting action, in some preferred embodiments a fixing action, one may preferably be formed directly by the support structure, i.e., in one piece with the latter. A counteracting support shoulder lying axially opposite this support shoulder may preferably be formed by a support element which is releasably connected to the support structure and which forms an element for closing off a receiving compartment for the container. The support structure and the releasable support element have interacting engaging means which together form a releasable connection, but one which is secure in the connected state. In some embodiments, the two engaging means are preferably threads, such that the releasable support element can be screwed into the receiving compartment or screwed onto the receiving compartment. In some embodiments, the releasable support element preferably forms what is the front support shoulder in the delivery direction. In some embodiments, the container may be inserted into the receiving compartment from the rear, so that in this case the front support element is preferably formed in one piece by the support structure or can be connected non-removably to the support structure, while the rear support element in this case is preferably connected to the support structure releasably, but in a manner that is secure in the connected state. The receiving compartment can also be designed such that the container is inserted from the side. For this purpose, the support shoulder and the counteracting support shoulder can be made elastically resilient to a slight degree, so that the container can be clipped into place, for example. The support structure has the inventive property or quality, namely that of thermal expansion adapted to the container, at least in its axial section between the support shoulder and the counteracting support shoulder for the container.

In a preferred development of the present invention, the support structure also axially supports the delivery means or at least a component of the delivery means. In an axial section extending from the support location of the delivery means or of the at least one component to what is a front end of the delivery means or of the component in the delivery direction, the support structure has an axial thermal expansion which differs by at most about 500%, and more preferably by at most about 200%, from the axial thermal expansion of the delivery means or of the at least one component, the axial thermal expansion of the delivery means being measured over its aforementioned axial section.

The delivery means or mechansim can be in abutment on the support structure in and counter to the delivery direction and thus be axially fixed by the support structure, as has been described in respect of the container. In another embodiment, the delivery means is axially supported by abutment on the support structure only in one direction and is supported via a spring device in the other direction. The spring device can advantageously be used to eliminate or at least reduce an axial play of a rotation member of the delivery means.

If the administering device is equipped with a force sensor in order to be able to detect an occlusion and/or a leakage in a part of the device conveying the product, then the force sensor can form a spring device in the above sense. To be able to detect an occlusion situation and/or a leakage situation, the delivery means is supported on the support structure counter to the delivery direction via the force sensor. The delivery means is not connected fixedly as such to the support structure, and instead, at least when product is delivered or an attempt is made to deliver product, it presses on a contact surface, which is preferably punctiform, against the support structure or a contact element connected axially rigidly to the support structure. The force sensor can be axially rigid, for example designed as a piezo element, but it may be more preferable for the force sensor to be elastically resilient in the axial sense. In a preferred embodiment of this kind, the delivery means is mounted so as to be movable, counter to an elastic restoring force of the force sensor, relative to the support structure counter to the delivery direction and thus axially floats on the support structure via the force sensor. The force sensor can be an elastic flexion element provided with strain gauges so that it is possible, via the strain associated with the elastic deflection, to pick up the axial reaction force of the delivery means acting on the support structure. Alternatively, a rigid sensor element could be supported with axial resilience, and, for example, the axial excursion could be measured as distance. Within the meaning of the invention, force sensor is understood as any sensor from whose measured values it is possible to draw conclusions regarding the force or the pressure with which the delivery means acts on the product in the container.

In some embodiments, the coupling between the drive member and the output member is preferably a flank engagement formed by the drive member and the output member each having at least one engagement flank. Preferably, the at least one engagement flank of the drive member is formed directly on the drive member, and the at least one engagement flank of the output member is formed directly on the output member. The drive movement can be an axial movement, as may be the case especially when the device is an injection appliance. More preferably, however, the drive movement is a rotation movement, in this case generally about an axis along which the output member executes the output movement.

In the output movement, the output member can act directly on the product located in the reservoir, for example by itself forming a reciprocating piston or by being connected permanently to a reciprocating piston. However, it can also simply press or abut in a loose state against a reciprocating piston. A configuration is also possible in which the output member acts only via a transmission member or several transmission members on a delivery element, for example a reciprocating piston, which acts directly on the product when it executes the output movement. Thus, the delivery means can have a telescoping design, as is described in DE 197 17 107 A, to which reference is hereby made. In such a design, two adjacent telescope stages located in flank engagement in each case form a drive member and an output member according to the present invention.

In a preferred embodiment of the present invention, the support structure, in an axial section extending from the flank engagement to what is a front end of the output member in the delivery direction, has an axial thermal expansion that differs from the axial thermal expansion of the output member by at most about 500% and preferably by at most about 200%. The extent of the axial section of the support structure is here considered in relation to a frontmost position of the output member in the delivery direction.

For production reasons, flank engagements, such as are known from thread and/or tooth engagements, have an axial play transverse to the engagement flanks, and this axial play may impair the metering accuracy, for example if a siphoning effect, i.e., a suction situation in the container, takes place during a dispensing operation.

In a further development, however, a second device for reducing play is provided. In some embodiments, the second device may be in adjustment engagement with the drive member and also with the output member, in which the device for reducing play is moved relative to the output member and the drive member into an adjustment position and is secured in the adjustment position so that the axial play inherent to the flank engagement is reduced, compared to the known couplings based on flank engagement, or is substantially completely eliminated. The adjustment engagement with one of the two members, namely drive member and output member, corresponds to the flank engagement between the drive member and the output member. The other adjustment engagement defines the displacement movement of the play-reducing device along its displacement path. The length of displacement available in this adjustment engagement may preferably be sufficiently long that the device for reducing play, in its adjustment position, is not in abutment with the member in question but still within the length of displacement available in this engagement. The two adjustment engagements can also be of the same kind or completely the same. In the latter case, they jointly define the course of the displacement path.

In some embodiments, the adjustment engagement with the drive member is preferably obtained with a form fit and force fit, and it is particularly preferably a thread engagement. The same applies as regards the adjustment engagement with the output member. Forming both the adjustment engagements of the second device for reducing play as thread engagements is expedient when the flank engagement between the drive member and the output member is also a thread engagement, as is preferred in some embodiments of the present invention. However, it is also possible, for example, for the adjustment engagement that defines the displacement movement to be configured as engagement of an engagement member of the play-reducing device in a guide track purely with a form fit and, by means of an elasticity force, to form the other of the two adjustment engagements with a form fit and force fit. In some preferred embodiments, the adjustment engagement defining the displacement movement is continuous in the sense that the axial play between the drive member and the output member can, in the adjustment engagement, be decreased continuously from its production-related initial value to a value of zero, as is permitted for example by the thread engagement. The thread engagement provides the further advantage that the device for reducing play is axially supported by the adjustment engagement itself in each position assumed along the displacement path.

In preferred embodiments, the second device for reducing play is secured on one of the members, namely one of the drive member and output member, against axial movements relative to the member in question. The securing can be obtained by the device for reducing play moving along with the drive movement when the securing is between the drive member and the device for reducing play, and moving along with the output movement when the securing is between the device for reducing play and the output member.

In the illustrative case of thread engagement, the second device for reducing play can be secured in the adjustment engagement in the adjustment position simply by self-locking. However, in some embodiments, the device for reducing play is preferably secured cohesively in its adjustment position in the secured adjustment engagement. This also applies if it is a thread engagement. The cohesive securing may take place in the adjustment engagement with the drive member. However, securing on the output member would in principle also be possible with kinematic reversal. Instead of the securing being done only in one of the two adjustment engagements, the securing can also be done by the device for reducing play cooperating with the drive member and the output member, in this case by the device for reducing play being elastically supported both on the drive member and/or also on the output member.

The preceding discussion does not exclude the possibility that one of drive member and output member is a toothed rack and the other is a carrier engaging in the toothed rack. Such rack-and-pinion arrangements or gears are known, for example from injection pens, so that it is not necessary to go into details. For a rack-and-pinion gear of this kind, the second device for reducing play can be formed by means of a further carrier, such that two carriers engage in the same series of teeth. In a rack-and-pinion gear of this kind, it is also possible to adjust the axial spacing of the two carriers in order to reduce the axial play that is present from the outset for tolerance reasons.

If the delivery means is able to telescope, a second device for reducing play according to an embodiment of the present invention is advantageously provided between each pair of telescope stages in engagement between the drive member and the output member, preferably flank engagement. In the case of a telescoping delivery means, an axial section of the support structure having the inventive thermal expansion in relation to the delivery means advantageously extends from the front end of a frontmost output member to the location where the rearmost output member engages with a drive member of the delivery means.

In preferred embodiments of administering devices in accordance with the present invention, the drive member is a rotation member which is mounted so as to move in rotation about a rotation axis. The output member is a translation member that can move in translation in a translation direction. A rotary drive movement of the drive member in a drive direction effects the axial output movement of the output member in the delivery direction. If the administering device is an infusion appliance, the drive member that can move in rotation may preferably be supported such that it cannot move relative to a bearing body in and counter to the translation direction of the output member. Since the output member is supported counter to the delivery direction on the drive member, an undesired axial movement of the drive member would take place in reaction to the output movement of the output member, simply on account of the axial play that is unavoidable in the known rotary bearings and that affects its rotary bearing required for the rotation movement.

In another preferred development, a third device for reducing play is therefore provided for delivery means of this kind, in order to reduce or substantially eliminate the axial play inherent to the rotary bearing of the drive member. The rotary bearing comprises the bearing body which supports the drive member rotatably about its rotation axis. The bearing body can be made in several parts, said several parts being connected axially rigidly to one another, but it may preferably be made in one part. It can also be formed directly by the housing of the device. However, it may be preferable if the bearing body is formed separately and is inserted into the housing. In some preferred embodiments, moreover, the bearing body is a bearing sleeve which surrounds the drive member at least in an axial section.

In order to reduce the axial play of the rotary bearing, at least two axial support surfaces of the rotary bearing are connected axially rigidly to the bearing body, and at least two further axial support surfaces of the rotary bearing are connected axially rigidly to the drive member. In axially rigid connection, the support surfaces can be formed either directly by the bearing body or the drive member, or the support surface in question is formed by a separate body, which is then, however, connected axially rigidly or substantially completely rigidly, to either the bearing body or the drive member. In some preferred embodiments, at least one of the support surfaces is formed by the third device for reducing play which, in adjustment engagement either with the drive member or with the bearing body, is moved into such an adjustment position and axially secured in the adjustment position on the bearing body or in the drive member in such a way that the axial play of the rotary bearing is reduced or eliminated. If the drive member and the output member are stages of a telescoping delivery means, as it is described in DE 197 17 107 A, for example, then the rotary bearing forms the rotary bearing of the first stage of the delivery means.

The first and/or second and/or third devices for reducing play is/are, in some embodiments, preferably formed in one piece as a single adjustment member which is at least axially rigid in both adjustment engagements and corresponding to the axial play that is to be reduced. In the case of a multi-part device for reducing play, such a device for reducing play should be inherently axially rigid at least when it is secured in the adjustment position. Thus, for example, a two-part device for reducing play could have a first adjustment member which is in adjustment engagement with the drive member, and a second adjustment member which is in adjustment engagement with the output member. The two adjustment members would be displaced axially relative to one another into the adjustment position and, in the adjustment position, would have to be secured axially on one another or secure themselves automatically to one another in order to obtain the axial rigidity.

The invention functions advantageously with each of the devices for reducing play and with each possible combination of two of the devices for reducing play, and particularly advantageously with all three together.

The support structure described above in connection with the avoidance of axial play on account of thermal expansions has advantages even without the thermal expansion properties according to the present invention. Irrespective of this property, in some embodiments, the support structure can serve as support structure or bearing structure for the container and for the delivery means so that, in a housing formed by the support structure and a shell structure, the shell structure is exempted from the function of axial support or completely from the function of bearing the container and the delivery means and, in some embodiments, from all supporting and other bearing functions. Thus, in some embodiments, the support structure can be designed in such a way that the container, the delivery means and other components of the device, for example all the electronics, are axially supported and borne or carried by the support structure.

In a first assembly step in accordance with embodiments of the present invention, components supported on the support structure and borne or carried by it can advantageously be connected to the support structure before, in a further step, the shell structure, in the form of, for example, two shells, is then mounted around the support structure. The assembly work is very much simplified in this way. In particular, the shell structure no longer has to be designed with a supporting function, as was previously customary, but provides a protective function for the covered components of the device. Moreover, the shell structure can be formed free from a supporting function and free from any bearing function in respect of design, in particular handling comfort. The applicant reserves the right to obtain separate protection for a device with such a housing comprising support structure and shell structure, in particular for a device which is used for metered administration of a liquid product and which comprises at least the following components: a container for the product, a delivery means or mechanism which acts on the product located in the container and delivers product from the container by means of an axial output movement in a delivery direction, an inherently axially rigid housing support structure which axially supports the container and the delivery means by axially supporting the container with a front support location in the delivery direction and axially supporting the delivery means with a support location in and/or counter to the delivery direction, and a housing shell structure which covers at least quite a large part of the housing support structure. The device can advantageously be developed, within the meaning of the present invention, such that preferred embodiments of such a device are designed as described above for the invention.

Under the aspect of separation of axial supporting function and preferably any bearing function, on the one hand, and protective function and/or design function, on the other hand, the properties of thermal expansion of the support structure which are described in the present application with respect to the container can instead or also be related to the delivery means or mechanism or only axially moved components of the delivery means, while the properties of thermal expansion of the support structure which are described with respect to the container advantageously also apply in such embodiments, but do not necessarily have to apply.

BRIEF DESCRIPTION OF THE DRAWINGS

FIGS. 9a and 9b, shows components of the administering device in the illustrative embodiment of FIG. 6 in an exploded view, and FIG. 10 shows the translation member of the illustrative embodiment of FIG. 6.

DETAILED DESCRIPTION

Figure 1:
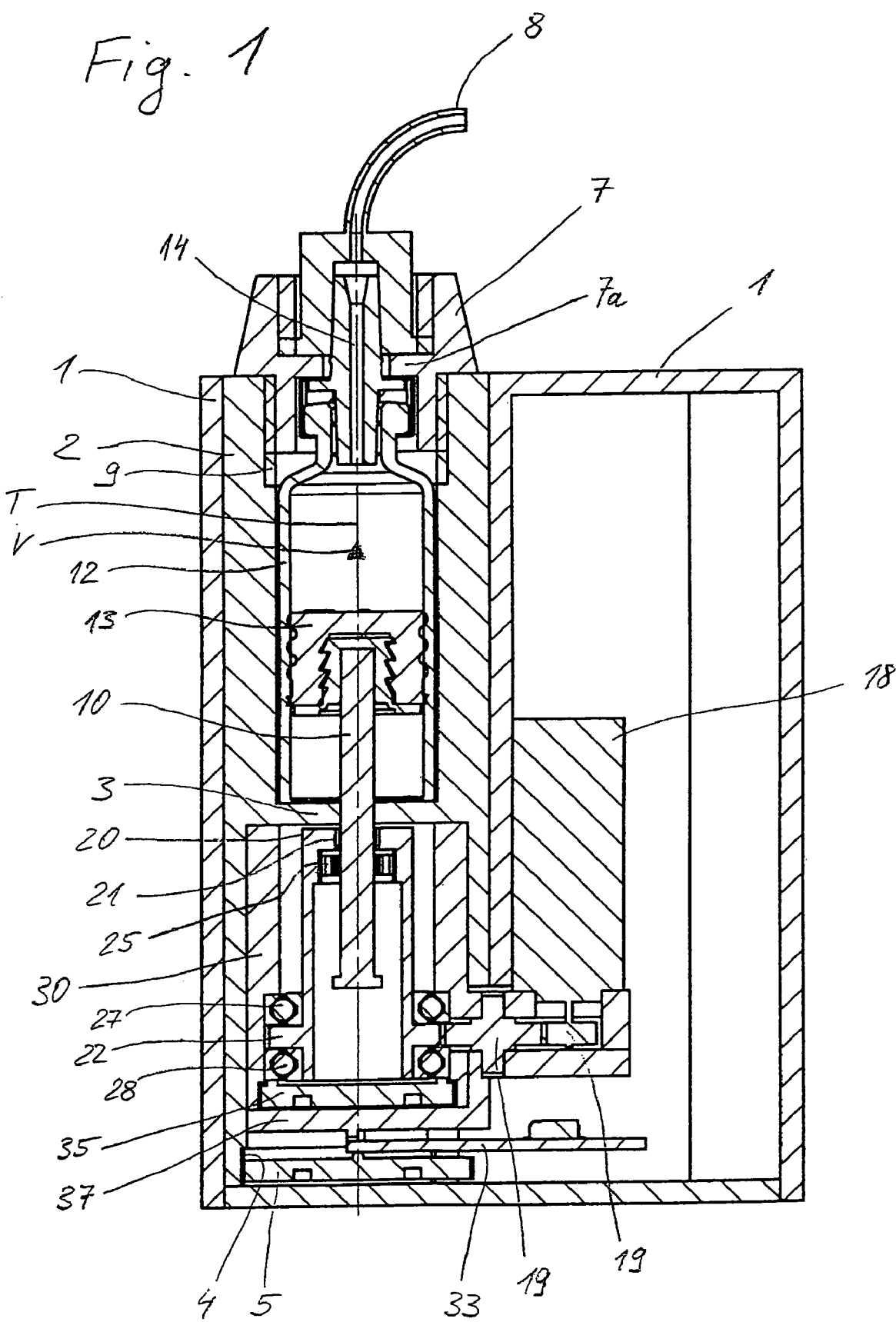
FIG. 1 is a longitudinal section through an administering device in one illustrative embodiment of the present invention.

An infusion appliance, representing an example of an administering device, is shown in longitudinal section in FIG. 1. The appliance has a housing with a first housing structure 1, and with a second housing structure 2, a container 12 filled with an injectable product, and a delivery means or mechanism which functions to deliver or force the product in metered amounts from the container 12 and through an adjoining catheter 8 in order to administer it. The administration can take place subcutaneously in particular, as is customary in the treatment of diabetes, for example. The first housing structure 1 surrounds the second housing structure 2 and is designated below as the shell structure 1. The second housing structure 2 supports components of the infusion appliance and is designated below as the support structure 2.

At one end, which way he referred to as the front end, the container 12 has an outlet 14 via which the interior of the container is connected to the catheter 8. In the container 12, a piston 13 is received in such a way that it can move along a translation axis T in a delivery direction V towards the container outlet 14. The container 12 is open at its rear end. However, the piston 13 seals the container 12 off at the rear end.

The shell structure 1 forms a fixed shell in which the support structure 2, which is formed in one piece by a support body 2, is inserted and secured and forms a chassis of the housing. The shell structure 1 and the support body 2 substantially form the housing of the device. The support body 2 forms a first receiving space in which the container 12 is fitted, and a second receiving space for the delivery means. The container 12 rests with its rear free edge abutting against a radially inwardly projecting support web 3 of the support body 2 forming a support shoulder. The first receiving space formed by the support body 2 has, at the front end, an opening through which the container 12 is inserted. After insertion of the container 12, the opening is closed with a lid 7. The lid 7 is screwed onto the support body 2, which is provided with a thread 9 for this purpose. The support body 2 and the lid 7 could, however, each be provided with another engaging means for releasable engagement, for example with cooperating catches. The lid 7 also forms the connection element between the catheter 8 and the outlet 14 of the container 12. The lid 7 has, for the support shoulder of the support web 3, a counteracting support shoulder on a counteracting support web 7a which presses against a front edge of the container 12 and thus presses the container 12 in abutment against the support web 3 so that the container 12 is axially fixed relative to the support body 2. The lid 7 thus forms a front closure element 7a, and the support web 3 forms a rear closure element 3 of the first receiving space. The first receiving space is further shaped in such a way that the container 12 has the correct position and orientation in relation to the translation axis T. As a result, the support body 2 supports the container 12 axially in and counter to the delivery direction V with a form fit, i.e. by contact with the webs 3 and 7a serving as abutments. In a comparable way, the delivery means is supported axially between other abutments of the support body 2.

The delivery means comprises the piston 13, an output member 10, a drive member 20 and a motorized rotary drive. The output member 10 forms a translation member of the delivery means, and the drive member 20 forms a rotation member of the delivery means.

The output member 10 is a piston rod, e.g., a piston rod provided with a thread. In the illustrative embodiment, the output member 10 is provided with an outer thread 11 which can be seen in the longitudinal section in FIG. 2. The output member 10 extends through the support web 3 so that it protrudes into the first receiving space and the second receiving space of the support body 2. At its front end, the output member 10 is screwed onto the piston 13. The screw connection is established upon insertion of the container. The support web 3 guides the output member 10 linearly along the translation axis T. The support web 3 secures the output member 10 against twisting relative to the support body 2. In the illustrative embodiment, the thread 11 is for this purpose interrupted by at least one axial groove or flat in which the support web 3 engages.

The drive member 20 is arranged within the second receiving space of the support body 2. It is rotationally symmetrical with respect to the translation axis T. It is sleeve-shaped and can therefore also be designated as drive sleeve. At a front end of the sleeve, the drive member 20 forms a radially inwardly projecting web through which the output member 10 extends. On the inwardly projecting web, the drive member 20 forms an inner thread 21 which is in a threaded engagement with the outer thread 111 of the output member 10.

The drive member 20 is mounted such that it is rotatable about the translation axis T, but not axially movable relative to the support body 2. In a rear area, it has a radially outwardly projecting circumferential web 22 which is provided with an outer toothing. The drive member 20 is moved in rotation about the translation axis T via the outer toothing. Its rotary drive derives from a torque motor 18 which is accommodated in a further receiving space. The further receiving space is formed by the shell structure 1 and is separated from the two receiving spaces of the support body 2. The motor 18 drives the drive member 20 via a toothed gearing with radial teeth 19, of which an output toothed wheel 19 meshes with the outer toothing of the drive member 20. The threaded engagement between the drive member 20 and the output member 10 and the linear guiding of the output member 10 means that, when the drive member 20 is moved in rotation, its rotary drive movement results in an axial output movement of the output member 10 in the delivery direction V. The product displaced by the piston movement is dispensed through the catheter 8 and in this way administered.

Like any threaded engagement, the threaded engagement as such between the output member 10 and the drive member 20 is also associated with an axial play. The metering accuracy of the dispensing operation is therefore associated with a degree of imprecision, at least to the extent of this inherent axial play. For example, in the event of suctioning of the piston 13 on account of siphoning, or in the event of mechanical jolts or pressure differences between the housing interior and the environment, it can happen that the flanks of the outer thread 11 of the output member 10 lift from the driving thread flanks of the thread 21. The exact axial position of the piston 13 is therefore uncertain, to the extent of the axial play of the threads 11 and 21.

However, in accordance with the present invention, a device for reducing the play is provided which is formed by an adjustment member 25 and which virtually or substantially eliminates the axial play between the output member 10 and the drive member 20.

Figure 2:
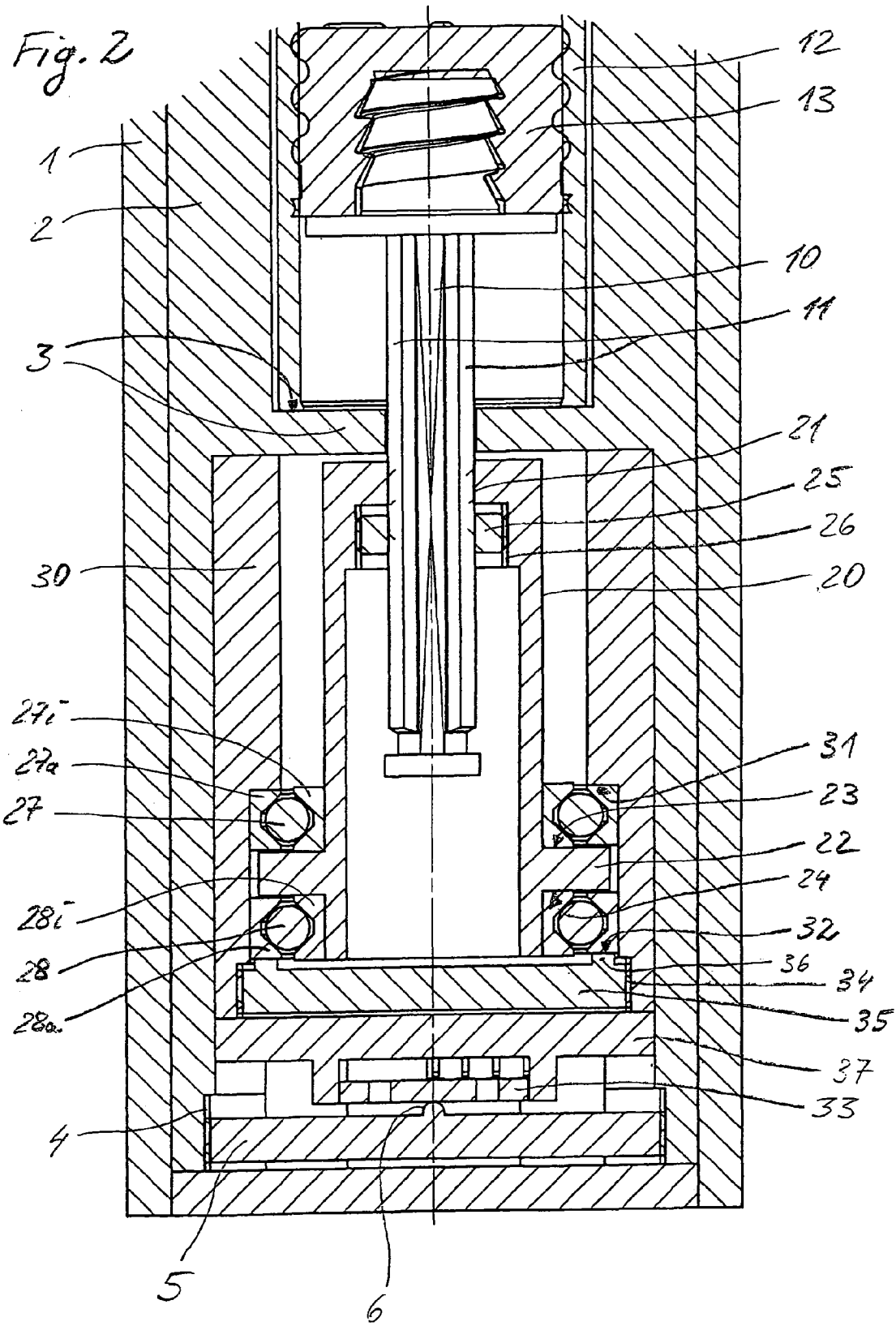
FIG. 2 shows part of the administering device of FIG. 1 in another longitudinal section.
Figure 3:
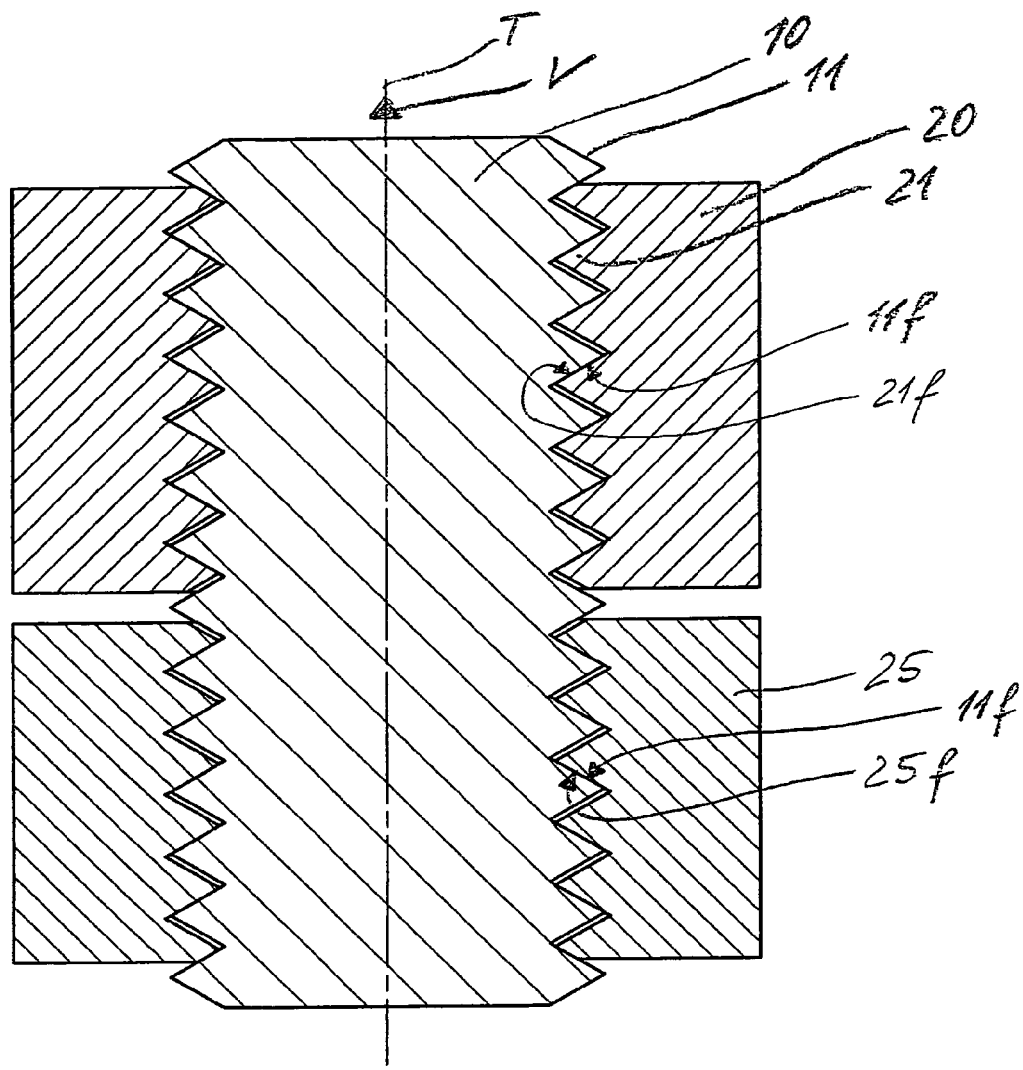
FIG. 3 shows an enlarged detail from FIG. 2.

The structure and action of the device for reducing play can be seen from FIGS. 2 and 3. The device for reducing play is formed by a one-piece adjustment member 25. The adjustment member 25 is in an adjustment engagement with the output member 10 and in a further adjustment engagement with the drive member 20. The adjustment member 25 and the two adjustment engagements are configured such that the axial play between the threads 11 and 21 is significantly reduced or eliminated.

In the illustrative embodiment, the adjustment member 25 is formed as a threaded nut with an inner thread and an outer thread. With its inner thread, the adjustment member 25 is in a threaded engagement with the outer thread 11 of the output member 10. With its outer thread, it is in a threaded engagement with an inner thread 26 of the drive member 20. The inner thread 26 is directed towards the outer thread 11 and formed axially immediately behind the thread 21. The inner thread and the outer thread of the adjustment member 25 lie at the same axial height, such that the adjustment member 25 can be axially thin and the device for reducing play can accordingly be made axially short, i.e., short along the translation axis T. The inner thread 26 may be sufficiently long that a secure adjustment engagement with the adjustment member 25 is ensured and the adjustment member 25 can additionally be displaced in this adjustment engagement such that the desired reduction of the axial play of the threads 11 and 21 can be provided. The inner thread 26 has a pitch allowing the adjustment member 25 to be displaced in threaded engagement with the inner thread 26 when threaded engagement exists between the threads 11 and 21 and between the thread 11 and the inner thread of the adjustment member 25.

FIG. 3 shows an enlarged representation of the threaded engagement of the threads 11 and 21 and the adjustment engagement between the thread 11 of the output member 10 and the inner thread of the adjustment member 25. The inner thread of the adjustment member 25 has the same pitch as the outer thread 11. In some embodiments, the pitch of the outer thread of the adjustment member 25 and of the inner thread 26 is preferably greater or smaller than the pitch of the threads 11 and 21, but so slight that the displacement of the adjustment member 25 in the adjustment engagement is possible.

For the reduction of axial play, the adjustment member 25 in its adjustment engagement with the output member 10 is set in such a way that its rear thread flanks 25f in relation to the delivery direction V are in contact with the front thread flanks 11f of the outer thread 11, while at the same time the front flanks 21f of the driving thread 21 are in contact with the rear flanks 11f of the thread 11 of the output member 10. For this purpose, the adjustment member 25 in its adjustment engagement with the drive member 20 is displaced relative to the drive member 20 counter to the delivery direction V until this state of flank contact is established. In this state, the adjustment member 25 is fixed on the drive member 20 and thereby secured. In an illustrative embodiment, the securing is produced adhesively by an adhesive agent being introduced into the adjustment engagement of the adjustment member 25 with the drive member 20. Other possibilities of cohesive connection between the adjustment member 25 and the drive member 20 are also conceivable, for example, sonic or laser welding in the adjustment position. If the inner thread 26, as in preferred embodiments, has a pitch different than the threads 11 and 21, the axial securing can be achieved by this alone or in combination with a cohesive connection. The adjustment position should be chosen such that the reduction in play causes no pressing forces, or at any rate no practically relevant pressing forces, to be exerted on the output member 10. The adjustment position is therefore chosen such that, in the threaded engagement of the threads 11 and 21, a very slight residual play remains, but one which is less or much smaller than the thread play inherent to this engagement alone, i.e. without reduced play.

In an illustrative embodiment, the adjustment position of the adjustment member 25 is chosen such that the thread 21 remains the driving thread of the drive member 20. The adjustment position could also be chosen, however, such that during adjustment the adjustment member 25 is moved against the rear thread flanks of the thread 11 and in this case the adjustment member 25 assumes the forward drive of the output member 10. Preference is given, however, to the adjustment position of the adjustment member 25 chosen for the illustrative embodiment and shown in FIG. 3.

Figure 4:
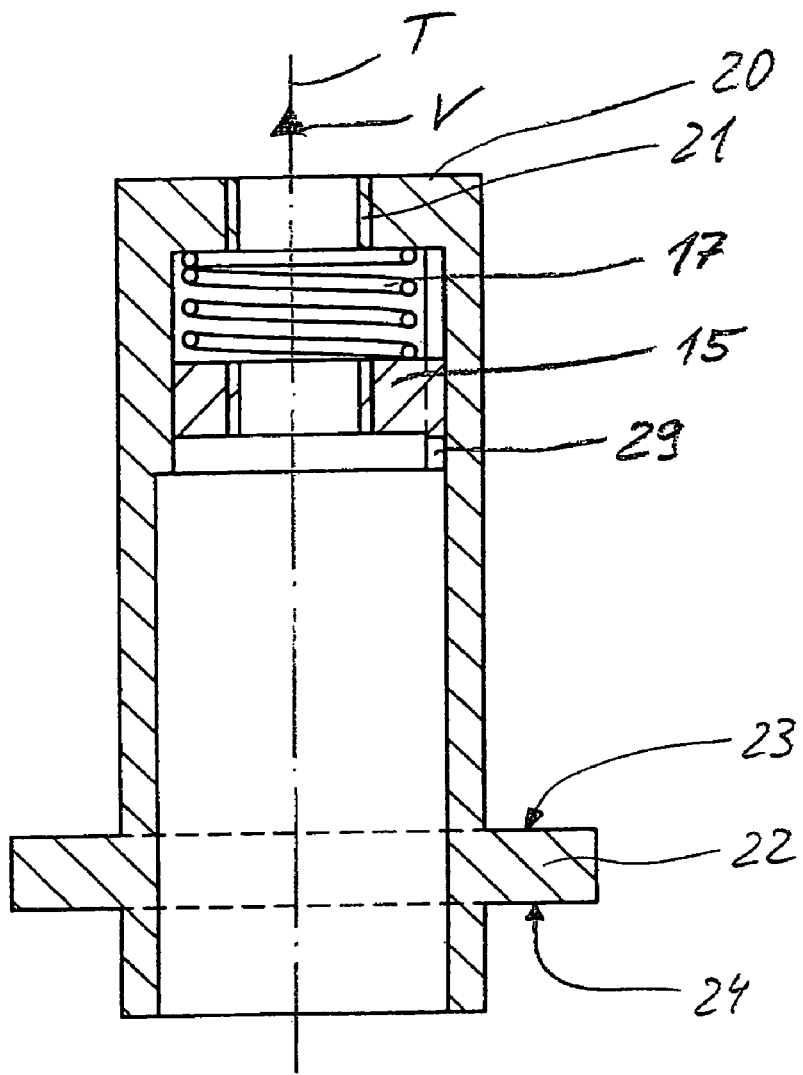
FIG. 4 depicts a device for reducing play in an alternative configuration.
Figure 5:
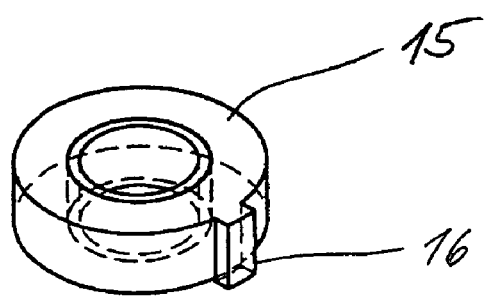
FIG. 5 shows an adjustment member of the device for reducing play from FIG. 4.

An alternative illustrative embodiment of a device for reducing play can be seen in FIGS. 4 and 5. Compared to the components of the illustrative embodiment in FIGS. 1 to 3, only the drive member 20 and the adjustment member, identified by 15 in the alternative illustrative embodiment, are modified, whereas the other components, in particular the output member 10, are unchanged. A further difference is that the alternative device for reducing play additionally comprises an elastic restoring element 17 in the form of a mechanical compression spring.

The adjustment member 15, like the adjustment member 25 before, is inserted into the sleeve forming the drive member 20. However, the adjustment member 15 is connected to the drive member 20 such that it is displaceable in an axially linear movement and is secured against twisting. The adjustment engagement of the adjustment member 15 with the drive member 20 therefore comprises a linear guide. The linear guide is formed by an axial, straight guide track 29 on the circumferential inner surface of the output member and by an engagement member 16 (FIG. 5) of the adjustment member 15 engaging in the guide track 29. The guide track 29 is limited in the delivery direction V by the radially inwardly projecting web of the drive member 20 that forms the driving thread 21. At the rear, the guide track 29 is open so that the adjustment member 15 can be pushed in. The restoring element 17 is also fitted beforehand. The restoring element 17 is supported in the delivery direction on the web of the drive member 20 forming the driving thread 21 and is supported counter to the delivery direction on the adjustment member 15. FIG. 4 shows this state before assembly with the output member 10.

For assembly, the adjustment member 15 is first inserted with the restoring element 17 into the drive member 20 into adjustment engagement with the guide track 29 and is pressed with a certain force against the restoring element 17. The output member 10 is then initially screwed onto the adjustment member 15 and then onto the driving thread 21. In the adjustment engagement, the rear thread flanks of the inner thread of the adjustment member 15 press with an elasticity force against those thread flanks of the thread 11 of the output member 10 that point in the delivery direction V. As a result, for the threaded engagement of the threads 11 and 21 via the two adjustment engagements of the adjustment member 15, the same state is obtained as is shown in FIG. 3. In the alternative device for reducing play, the adjustment member 15 is thus secured in the adjustment position by the elasticity force of the restoring element 17.

The infusion appliance in the illustrative embodiment has as a particular feature, but one known in principle from DE 198 40 992 A, an occlusion detection mechanism, which is also inherently subject to axial play, thus detracting from the metering accuracy. This inherent second axial play has its cause in the fact that the entire delivery means, in particular the output member 10 and the drive member 20, is supported axially on the support body 2 via a sensor 33. The sensor 33 is used to determine the force necessary for moving the piston 13 along the translation axis T. The sensor can, for example, be based on strain measurement. The sensor 33 is used to measure a physical parameter representing the liquid pressure in the container 12, in order to detect any occlusion or any leakage as early as possible during the administration of the product. As regards the occlusion detection and/or leakage detection and the sensor 33, the following deals only with those aspects concerning the axial play, and in other respects reference is made by way of example to DE 198 40 992 A.

For the occlusion detection and/or leakage detection function and/or mechanism, the delivery means, as has already been mentioned, is axially supported via the sensor 33. This means that the drive member 20, on which the output member 10 is axially supported in the driving engagement of the threads 11 and 21, is not connected in an axially rigid manner to the support body 2, but is instead mounted so as to be able to move axially relative to the support body 2, to be able to determine the liquid pressure in the container 12, or more precisely the differential pressure with respect to the environment. To obtain the axially movable bearing, the drive member 20 is mounted rotatably in a bearing body 30 and is axially secured on the bearing body 30. The bearing body 30 is inserted into the second receiving space of the support body 2 and secured against twisting. The support body 2 guides the bearing body 30 axially through sliding contact. The bearing body 30, and together with it the output member 10 and drive member 20, is supported axially on the support body 2 via the sensor 33 such that the sensor 33 picks up all the axial force acting between the bearing body 30 and the support body 2 and directed counter to the delivery direction V. In the delivery direction V, the bearing body 30 abuts against the support body 2. The bearing body 30 also supports the motor 18 and the gear 19 of the delivery means. In the illustrative embodiment, it is for this purpose provided with a lateral extension piece which projects through a lateral aperture of the support body 2 into the lateral receiving space of the housing shell structure 1, which lateral receiving space accommodates the motor 18, a control means and, if appropriate, a further appliance management system. For this purpose, the jacket of the substantially hollow-cylindrical support body 2 is provided with an aperture through which the sensor 33 also protrudes with a sensor attachment face at which it is connected to the control means and to a display.

The sensor 33 forms an elastic boom which is clamped firmly at both ends. The holder for the sensor 33 serves as an integrally formed sensor carrier 37 which is guided with axial sliding by the support body 2 and abuts, via a contact point 6 and the sensor 33, against the rear edge of the aperture of the bearing body 30 or if appropriate is fixedly connected to the bearing body 30. Since the sensor carrier 37 then also participates in each axial movement of the bearing body 30, if only abutment contact exists, it is attributed to the bearing body 30 and thus to the delivery means.

To substantially eliminate the axial play between the support body 2 and the bearing body 30, or at least to reduce it to an extent that can be tolerated in respect of the metering accuracy or that is no longer detectable in practice, a contact adjustment or compensation element 5 is provided which serves as an adjustment member 5. The adjustment member 5 forms the contact point 6 for the sensor 33. The contact point 6 comprises a cam which protrudes on the translation axis T from the front face of the adjustment member 5 in delivery direction V. The bearing body 30 is axially supported via the sensor 33 only in a quasi-punctiform manner at the contact point 6 on the translation axis T.

The adjustment member 5 is in an adjustment engagement with the support body 2. In the illustrative embodiment, this adjustment engagement is also a threaded engagement, namely between an inner thread 4 at the rear end of the support body 2 and a corresponding outer thread of the adjustment member 5. The adjustment member 5 is a circular cylindrical disc whose axial thickness is selected substantially exactly such that it is provided on its outer circumference with a sufficiently long threading for sufficiently secure adjustment engagement.

The adjustment position of the adjustment member 5 is chosen such that the bearing body 30 is in abutment against the support body 2 in the delivery direction, and at the same time the contact point 6 touches the rear face of the force sensor 33. The inner thread 4 of the support body 2 is sufficiently long to screw the adjustment body 5 in and to be able to adjust it in the adjustment engagement as far as this adjustment position. The adjustment position may preferably be chosen such that a calibration curve of the calibrated sensor 33 is not changed, in particular in such a way that the zero point of the calibration curve remains constant. The offset of the sensor 33 is therefore in other words "zero" when the pressure of the liquid in the container 12 corresponds to the ambient pressure. An offset is obtained upon priming of the infusion appliance. In principle, however, the adjustment position can also be chosen such that an offset is already obtained in the adjustment position before priming. This adjustment offset should be smaller than the offset obtained upon priming. The term "priming" designates the procedure by which the product-conveying parts, including an outlet point of the catheter 8 that can be formed by an insert cannula or a soft cannula, are filled completely with the product.

In its adjustment position, the adjustment member 5 is secured on the support body 2, in some preferred embodiments, cohesively connected to the support body 2. The cohesive connection can be obtained for example by laser welding or, in some preferred embodiments, by an adhesive agent introduced into the adjustment engagement.

Even without occlusion detection and/or leakage detection, an axial play is inherent not only to the threaded engagement between the output member 10 and the drive member 20, but also to the rotary bearings, such as are known from conventional infusion appliances.

To reduce the axial play in the rotary bearing of the drive member 20, adjustment or compensation is provided by an adjustment member 35. The adjustment member 35 is in an adjustment engagement with the bearing body 30. This adjustment engagement is also a threaded engagement. Like the adjustment member 5, the adjustment member 35 is also a flat, disc-shaped screw with an outer thread. At the rear end of the bearing body 30, the adjustment member 35 is screwed into the bearing body 30, which for this purpose forms an inner thread 34 in adjustment engagement with the outer thread of the adjustment body 35. The adjustment member 35 is arranged in such a way that, beyond the forces arising from the rotary bearing, no other external forces may act on the adjustment member 35.

For the axial supporting and securing of the drive member 20, the bearing body 30 forms a first support surface 31 oriented counter to the delivery direction V, and the adjustment member 35 forms a second support surface 32 facing towards the support surface 31. The drive member 20 forms, on its web 22, a third support surface 23 which is oriented in the delivery direction V and faces towards the first support surface 31, and a fourth support surface 24 which is oriented counter to the delivery direction V and faces towards the second support surface 32. A ball bearing 27 is held axially between the two support surfaces 31 and 23, and a further ball bearing 28 is held axially between the support surfaces 32 and 24. Each of the ball bearings 27 and 28 forms a radial bearing and, via the support surfaces 31 and 23 and also 32 and 24, an axial bearing. The ball bearings have, in the customary manner, an inner bearing ring and an outer bearing ring which are able to rotate relative to one another about the translation axis T and between which in each case a plurality of balls are arranged which transmit the radial and axial forces between the bearing rings. In the ball bearing 27, the inner bearing ring is indicated by 27i and the outer bearing ring by 27a. The ball bearing 28 correspondingly has an inner bearing ring 28i and an outer bearing ring 28a. The inner bearing rings 27i and 28i are radially supported on the outer circumferential surface of the drive member 20, and the outer bearing rings 27a and 28a are radially supported on the opposite inner jacket surface of the bearing body 30.

For the axial clamping of the ball bearings 27 and 28, the adjustment member 35, in its adjustment position, is pressed with a slight axial force against the outer bearing ring 28a. The adjustment member 35 and the ball bearing 28 are in contact only with the outer bearing ring 28a and the second support surface 32. The second support surface 32 is a circumferentially closed annular end face of an annular web 36 concentric to the rotation axis T, which annular web 36 protrudes in the delivery direction V from the front face of the adjustment member 35. The annular end face could also have interruptions. Similarly, the support surface 32 could be formed by individually protruding cams.

The outer bearing rings 27a and 28a have axially no contact with the support surfaces 23 and 24 of the drive member 20. The inner bearing rings 27i and 28i have axially no contact with the support surfaces 31 and 32. The axial force flow through the rotary bearing therefore runs exclusively via the contact of the support surfaces 31 and 32 with the respectively facing outer bearing ring 27a, 28a and the contact between the support surfaces 23 and 24 and the respectively facing inner bearing ring 27i, 28i. The axial force within the ball bearings 27 and 28 is therefore transmitted substantially exclusively by the balls. In this way, apart from manufacturing tolerances of the ball bearings 27 and 28, a rotary bearing is obtained which is virtually and/or practically free of play in the axial sense.

The adjustment member 35 is secured in its adjustment position like the adjustment members already described. The securing on the bearing body 30 is likewise preferably a cohesive connection and can in particular be effected by an adhesive agent which is introduced into the adjustment engagement. However, other cohesive connections, for example sonic or laser welding, or other suitable methods or structures, are also possible. As with the other adjustment members, the securing is effected in the adjustment engagement itself.

As regards the adjustment engagements, it should also be noted that the axial lengths of the paths of displacement of the adjustment members 5, 15, 25 and 35 in the adjustment engagements are each of such length that the respective adjustment member, when displaced into the adjustment position, cannot come into abutment contact against the body with which it is in the adjustment engagement, which blocks further displacement in the same direction.

In conventional infusion appliances and also in conventional injection appliances, a further source of axial play that detracts from metering accuracy is the large difference between the axial thermal expansion of the housings and the axial thermal expansion of the reservoir containers used. The housings are normally produced from plastic by injection moulding, while the containers are in most cases glass bodies. The coefficients of thermal expansion of these materials generally differ approximately by a factor of 10, i.e., a whole order of magnitude. For axial compensation of these differences in thermal expansion, the containers in the conventional appliances are supported on the housings with elastic resilience in the axial sense. In the temperature range in which the appliances are used, which range at least covers temperatures from −20° C. to 40° C., the positions between the delivery means and the containers therefore change axially to an extent that has an appreciable effect on the metering accuracy.

This axial play, and its negative impact on metering accuracy, is countered by the support body 2 having, in the axial direction, a thermal expansion factor or capability, inherently or otherwise provided, which is much closer to the axial thermal expansion of the container 12 than is the case with the housings of conventional appliances. Thus, the support body 2 can be made from a material whose coefficient of thermal expansion differs by a factor of approximately 5 from the coefficient of thermal expansion of the material of the container 12. It is more preferable if the coefficients of thermal expansion are as close as possible to one another or even identical. Structural measures are also conceivable, for example manufacturing the support body 2 as a composite body which includes several materials within the composite, for example stiffening bodies that are embedded in plastic and that obstruct the thermal expansion of the plastic material in the axial direction. Preferred materials for obtaining favourable thermal expansion have a coefficient of thermal expansion of $30 \times 10^{-6}$/K or less in the temperature range in which they are used. The materials preferably have a thermal expansion that is uniform in all directions. However, a support structure in the form of a composite body will by nature have an irregular thermal expansion, relative to the whole composite body, so that in such a case only the axial thermal expansion and the coefficient of axial thermal expansion are meant.

Some of the preferred materials for constructing infusion appliances and injection appliances are listed in the following table, together with their coefficients of thermal expansion $\alpha$ in the temperature range within which they are used:

| Material | Coefficient of thermal expansion $\alpha$ in $10^{-6}$/K |
| --- | --- |
| Brass | 18 to 19 |
| Steel | 10 to 12 |
| Aluminium | 23 to 24 |
| Polyamide PA | 100 to 140 |
| Polyoxymethylene POM | 110 to 130 |
| Polyethyleneterephthalate PET | 70 |
| Polycarbonate PC | 70 |
| Polytetrafluoroethylene PTFE | 60 to 200 |
| Acrylonitrile/butadiene/styrene ABS | 80 to 110 |
| Glass | 5 to 10 |
| Hard rubber | 75 to 100 |

By means of a support body 2 or, more generally, a support structure 2 made, for example, of aluminium or an aluminium-based alloy, it is already possible to achieve a considerable improvement over those plastic materials which in terms of thermal expansion come closest to the container material, preferably glass, because the coefficient of thermal expansion of aluminium is smaller, approximately by a factor of 3, than the coefficient of thermal expansion of the plastic materials that come closest to the container material in terms of the coefficient of thermal expansion. A further improvement can be achieved by using a brass material. If the support structure is made of steel, or if it has steel components arranged in such a way that the axial thermal expansion is critically influenced by the steel components, it is even possible, in the most favourable case, to achieve an identical thermal expansion, with appropriate choice of the glass material. If the support body 2 or more generally a support structure 2, which of course also assumes an axial support function like the support body 2, is formed as a composite body, then stiffening bodies, for example axial fibres incorporated into a plastic matrix, can provide a comparably favourable thermal expansion behaviour, if the stiffening body or bodies have a thermal expansion as described above.

The multi-part design of the housing, in the illustrative embodiment the two-part design, can in principle even be dispensed with if the housing shell, in the illustrative embodiment the shell structure 1, has a thermal expansion according to the invention. In such a design of a housing shell, it is preferable if the housing shell is formed as a composite body, for example as a plastic matrix with embedded stiffening bodies, such as, in particular, axially oriented metal fibres or other suitable material.

Even though a support structure is already advantageous which only supports the container axially, it is more advantageous if such a support structure extends over the greatest possible length measured in the delivery direction V of the piston 13. The support structure, for example as the support body 2, should additionally provide axial support for the delivery means in both directions, too. It is also particularly expedient if the delivery means as a whole also has an axial thermal expansion as close as possible to the axial thermal expansion of the support structure, for example by the support structure and the components of the delivery means being made from the same material or, if appropriate, from different materials that have axial thermal expansions as close as possible to one another. Advantageously, the output member 10 or the drive member 20 has, or preferably both of these components have, substantially the same axial thermal expansion as the support body 2, i.e., a thermal expansion which differs at most by a factor of approximately 5 and preferably by less than a factor of 5, preferably by at most a factor of 2 or even less, from the axial thermal expansion of the support body 2 and which is ideally identical.

The greater the axial length spanned by a one-part support structure or jointly by the several support bodies of a multi-part support structure, the smaller is the axial play attributable to different axial thermal expansions. Plastic parts of conventional type have to span very short axial lengths in this case. The shorter the axial lengths spanned by conventional plastic parts, the smaller is the axial play attributable to different thermal expansions. It is particularly expedient, as in illustrative embodiments of the present invention, if such a support body, or if appropriate several support bodies arranged axially in succession, is or are provided whose axial thermal expansion is close to that of the container and/or of the delivery means. The supporting means of the support body which secure the container and/or the delivery means axially on the support body or on the support bodies should be formed in one piece by the respective support body or be connected to the respective support body in such a way that they are not axially movable relative to the support body, such as, for example, by the pair of webs 3 and 7a, the pair comprising support web 3 and adjustment member 5, and the pair comprising adjustment member 35 and support surface 31.

The support body 2 is a comparatively simple sleeve body which is inserted into the shell structure 1 and is provided for the bearing of the mutually axially movable parts and thus for axial stiffening. The shell structure 1 itself can be produced in the customary manner from plastic by injection moulding. The shell structure 1 comprises two parts, namely a top part and a base part. The top part forms the receiving chamber for the support structure 2 and for those components of the administering device that are optionally not supported by the support structure 2. The base part is a simple plate which is connected fixedly to the rear face of the top part and there closes the receiving chamber.

In some embodiments, the lid 7 is preferably made from the same material as the support body 2. This also applies to the bearing body 30, the two adjustment members 35 and 5, and the carrier disc 37, resulting overall in a support structure that is very homogeneous in respect of the axial thermal expansion. The lid 7 and/or the carrier disc 37 and/or the adjustment member 35 and/or the adjustment member 5 may be produced from one of the customary plastic materials.

Figure 6:
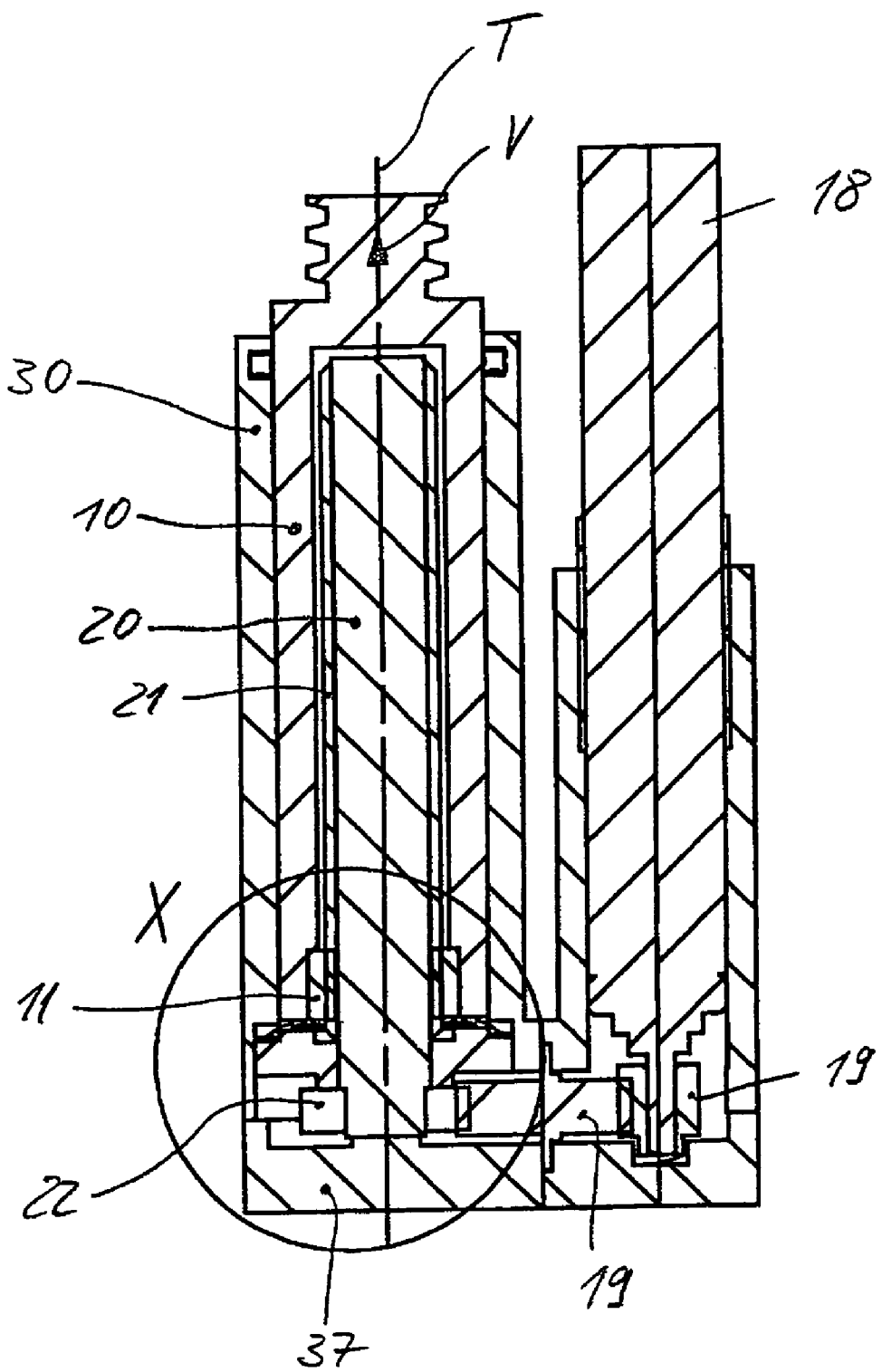
FIG. 6 is a longitudinal section through an administering device in another illustrative embodiment of the present invention.

FIG. 6 shows, in a longitudinal section, a bearing body 30 mounted in the same way as in the first illustrative embodiment, together with the components of an administering device that are supported by it, in accordance with a second illustrative embodiment, which is an infusion appliance. Those components of the second illustrative embodiment whose function and partly also whose construction are comparable with the components of the first illustrative embodiment have been given the same reference labels as in the first illustrative embodiment. Differences exist only in so far as are indicated below or as appear from the figures themselves. The statements concerning the first illustrative embodiment are intended also to apply to the embodiment of FIG. 6, unless anything is stated to the contrary.

The administering device in the second illustrative embodiment has a device for reducing play intended for eliminating or at least reducing the axial play between the rotation member 20 and the bearing body 30. In contrast to the first illustrative embodiment, the device for reducing play axially clamps the rotation member 20 directly against the sensor carrier 37. Moreover, in the second illustrative embodiment, the translation member 10 substantially surrounds the rotation member 20. The translation member 10 and the rotation member 20 are in threaded engagement with one another. For this purpose, the rotation member 20 is provided over most of its axial length with an outer thread 21, and the translation member 10 is provided with an inner thread 11 only at its rear end in relation to the direction of translation V. The translation member 10 is guided in an axially linear manner on the bearing body 30. As in the first illustrative embodiment, a motor 18, preferably an electric stepper motor, drives the rotation member 20 in a rotary movement about the rotation and translation axis T via a cylindrical gear with two toothed wheels 19 in radial engagement. For its drive, the rotation member 20 is again provided at its rear end with an outwardly toothed annular web 22 which is in radial engagement with the intermediate wheel 19 of the cylindrical gear for the rotary drive of the rotation member 20.

Figure 7:
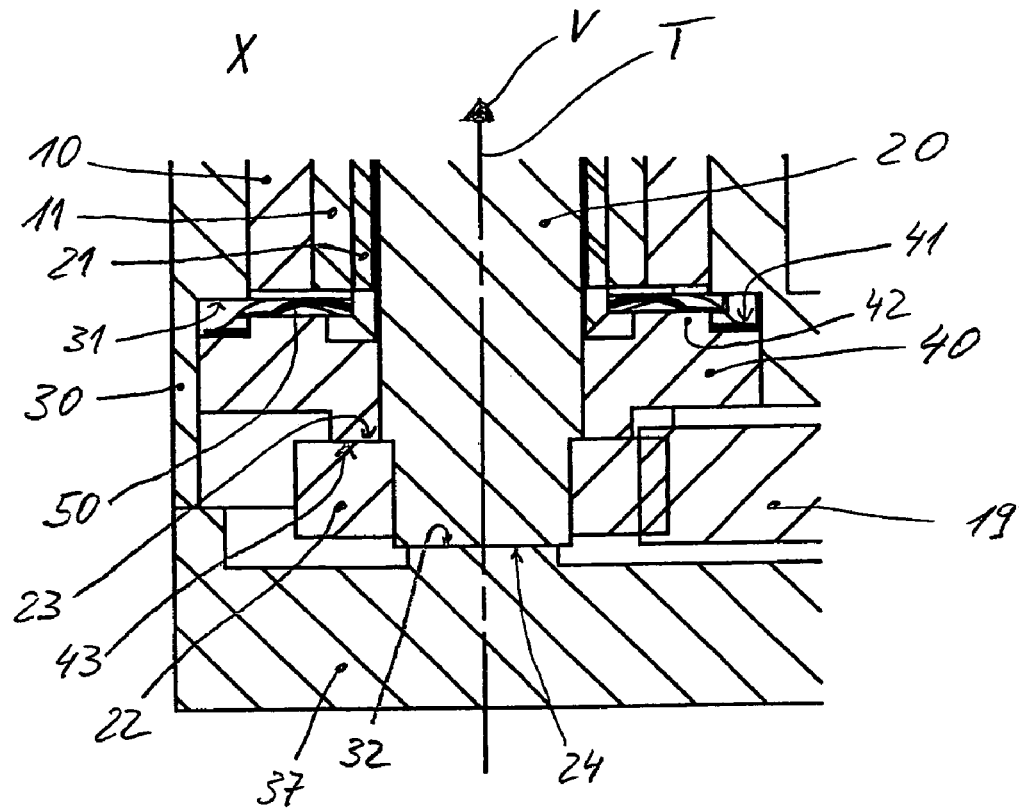
FIG. 7 shows a detail "X" from FIG. 6.

The rotary bearing of the rotation member 20 is shown in an enlarged view in FIG. 7. The rotary bearing in the second illustrative embodiment is formed as a simple slide bearing. The second support surface 32 of the sensor carrier 37 and the fourth support surface 24 of the rotation member 20 form a first slide pair surface of the rotary bearing. The two support surfaces 32 and 24 are in direct sliding contact with one another. The second support surface 32 is formed at the rear end of the rotation member 20. Protruding toward it from the sensor carrier 37, there is a short pedestal whose front face forms the second support surface 24. The pedestal frees the rotation member 20 from the sensor carrier 37. The formation of a pedestal permits more precise production of the second support surface 32. The third support surface 23 is formed in the manner of the support surface 23 in the first illustrative embodiment, namely by the front face of the annular web 22 that points in the translation direction T. The first support surface 31, facing axially towards it, is formed by the bearing body 30. However, the support surfaces 31 and 23 are radially offset from one another, i.e., they are not exactly in axial alignment. The radial offset is spanned by a transmission body 40, in the illustrative embodiment a transmission ring, which is arranged between the support surfaces 31 and 23. The transmission body 40 forms, on a front face, a front support surface 41 which lies in axial alignment opposite the first support surface 31 and which extends around the translation axis T and the rotation member 20, and it forms, on its rear face, a rear support surface 43 which lies in axial alignment opposite the third support surface 23. The rear support surface 43 is directly in abutment contact with the third support surface 23. A clear axial spacing remains between the first support surface 31 and the front support surface 41 facing towards it. An annular spring 50 is arranged between the two support surfaces 31 and 41 and bears axially on both support surfaces 31 and 41 with an axial pretensioning force.

Figure 8:
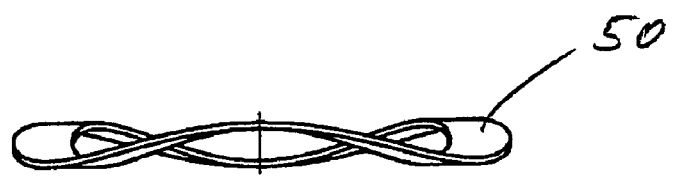
FIG. 8 shows a spring washer ring of a device for reducing play in the illustrative embodiment of FIG. 6, FIG. 9, including

The annular spring 50 is shown on its own in FIG. 8. It undulates about its perimeter and is made, for example, from spring steel. In the installed position, it bears alternately with its wave crests and wave valleys on the first support surface 31 and the front support surface 41 of the transmission body 40. Upon axial compression, it acts like a leaf spring.

As can be seen in particular from FIG. 7, the transmission body 40 not only serves to compensate for the radial offset, but also to centre the annular spring 50. For this purpose, the transmission body 40 is provided, on its front face, with an annular projection 42 about whose outer circumference the front support surface 41 extends, slightly set back axially.

The annular spring 50 and the transmission body 40 form the device or mechanism for reducing play in the second illustrative embodiment, since the transmission body 40 is axially movable relative to the bearing body 30. In some embodiments, the body is preferably guided in an axially linearly manner by the bearing body 30. In principle, however, it can move in rotation relative to the bearing body 30. Although the transmission body 40 can in principle be connected to the rotation member 20 in a manner fixed in terms of rotation, either by means of being joined thereto or by being designed in one piece with the rotation member 20, in some embodiments it is preferable if the transmission body 40, as in the illustrative embodiment, can move in rotation relative to the rotation member 20 and, even more preferably, is also axially movable. In this way, a further pair of slide surfaces of the rotary bearing is formed by the support surfaces 23 and 43 sliding directly on one another. The annular spring 50 is thus advantageously kept free from rotation movements.

In the second illustrative embodiment this provides, for the rotation member 20, an advantageously simple device for reducing play which, with sufficient pretensioning of the annular spring 50, eliminates any axial play between the rotation member 20 and the bearing body 30. In configurations in which the support surfaces 31 and 23 lie in axial alignment opposite one another, the transmission body 40 could be dispensed with. However, in order to keep the annular spring 50 free from rotation movements in these configurations too and/or to obtain an easy-to-produce centring for the annular spring 50 or also for another spring device generating the pressing force, the interposition of a transmission body in the manner of the transmission body 40 is then also of advantage.

FIG. 9, including FIGS. 9a and 9b, is an exploded view showing the bearing body 30, the rotation member 20, the transmission body 40 and the annular spring 50 in series along the imaginary translation axis, in a sequence suitable for one method of assembly in accordance with the present invention. FIG. 10 shows the translation member 10 on its own. In a first assembly step, the translation member 10 on its own can be inserted from behind into the bearing body, and the rotation member 20 can then be screwed into the translation member 10, or the threaded connection between the translation member 10 and the rotation member 20 can first be produced, and only then is the translation member 10 with the screwed-in rotation member 20 inserted into the bearing body 30. Before the rotation member 20 is screwed in, the transmission body 40 and the annular spring 50 are pushed via the outer thread 21 as far as the annular web 22 of the rotation member 20, after which the rotation member 20 is screwed into the translation member 10. After the translation member 10 and the rotation member 20 are arranged in the bearing body 30, the sensor carrier 37 is connected to the main part (shown in FIG. 9) of the bearing body 30 so that it closes the rear face of the bearing body 30 that is open for assembly purposes. The bearing body 30 and sensor carrier 37 are not movable relative to one another in the connected state. The connection is also configured such that the annular spring 50 is installed with a defined axial pretensioning force.

In the second illustrative embodiment, the threaded engagement of the threads 11 and 21 is formed as a simple threaded engagement, although, as in the first illustrative embodiment, it can also be readily formed to permit reduction of axial play by means of an additional device for reducing play.

It should also be noted that in the first illustrative embodiment a device for reducing or preferably eliminating axial play of the rotary bearing of the rotation member 20 can be formed as in the second illustrative embodiment, and that, conversely, the device for reducing play 35 based on the adjustment engagement can be provided in the second illustrative embodiment instead of the device for reducing play 40, 50. Combined forms are also conceivable. Thus, one of the roller bearings 27 and 28 could be arranged between one of the support surface pairs 31, 23 and 32, 24 or in each case one roller bearing between both support surface pairs, in which case the roller bearing or the two roller bearings would preferably each be arranged like the roller bearings 27 and 28 of the first illustrative embodiment, i.e., the annular spring 50 or an alternative spring would act only on one of the bearing shells of such a roller bearing.

Dispensing with the axially movable bearing and with the sensor 33, the bearing body 30 could be modified to form a housing with a seat for a reservoir 12 and could then serve directly as a shell structure, like the shell structure of the first illustrative embodiment. Such a shell structure can be formed like conventional housings. Alternatively, however, it can have the thermal expansion properties of the support structure 2 of the first illustrative embodiment, so that reference is made here to the explanations given in this connection with reference to the first illustrative embodiment.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for metered administration of a liquid product, said device comprising:
   a) a glass container for the product,
   b) delivery means which acts on the product located in the container and delivers product from the container by means of an axial output movement in a delivery direction, and
   c) an inherently axially rigid housing support structure formed as a sleeve-shaped body which supports the container in and counter to the delivery direction, wherein
   d) the housing support structure having, over the axial length of the container, an axial thermal expansion which, within a temperature range in which the device is used, differs by about 500% or less from the axial thermal expansion of the container.

2. The device according to claim 1, wherein the housing support structure is made of a material which, within the temperature range in which the device is used, has a coefficient of thermal expansion corresponding at least substantially to the coefficient of thermal expansion of the material from which the container is made.

3. The device according to claim 1, wherein the coefficient of thermal expansion of the material of the housing support structure and the coefficient of thermal expansion of the material of the container differ from one another by at most about 500%.

4. The device according to claim 1, further comprising a support shoulder oriented transversely with respect to the delivery direction and serving as an abutment for the container is formed in one piece by the housing support structure or in a releasable, axially rigid engagement with the housing support structure.

5. The device according to claim 4, further comprising a counteracting support shoulder oriented transversely with respect to the delivery direction and serving as a counter-abutment to the support shoulder for the container is in a releasable, axially rigid engagement with the housing support structure or is formed in one piece by the housing support structure.

6. The device according to claim 1, further comprising a support shoulder and the counteracting support shoulder cooperating to fix the container in and counter to the delivery direction.

7. The device according to claim 1, wherein the housing support structure forms a receiving compartment with a support shoulder projecting inwards transversely with respect to the delivery direction and with an opening which lies opposite the support shoulder and through which the container can be inserted into the receiving compartment, and in that the device has a closure element which, in a releasable engagement with an engaging means of the housing support structure, closes the opening of the receiving compartment and forms for the container a counteracting support shoulder lying opposite the support shoulder.

8. The device according to claim 7, wherein the housing support structure, in an axial section extending at least from the support shoulder to the counteracting support shoulder, has at least substantially the same thermal expansion.

9. The device according to claim 7, wherein the housing support structure, in an axial section extending at least from the support shoulder to the counteracting support shoulder, is formed in one piece.

10. The device according to claim 1, wherein the housing support structure axially supports the delivery means.

11. The device according to claim 10, further comprising a force sensor for at least one of occlusion detection and leakage detection, wherein the delivery means is supported on the housing support structure via the force sensor counter to the delivery direction.

12. The device according to claim 11, wherein the delivery means, counter to an elastic restoring force of the force sensor, is movable counter to the delivery direction relative to the housing support structure.

13. The device according to claim 11, the device further comprising a contact element against which the force sensor presses when the delivery means executes the output movement, wherein at least one of the contact element or the force sensor, in adjustment engagement with the housing support structure or with the delivery means, is moved into an adjustment position and secured in the adjustment position in such a way that an axial play between the delivery means and the housing support structure is reduced.

14. The device according to claim 11, wherein the housing support structure axially guides the delivery means.

15. The device according to claim 14, wherein the housing support structure in the delivery direction forms an abutment for the delivery means.

16. The device according to claim 15, wherein the housing support structure is formed in one piece, at least in an axial section which supports the delivery means in and counter to the delivery direction.

17. The device according to claim 1, further comprising a bearing body which axially supports the delivery means and which is axially guided by the housing support structure.

18. The device according to claim 17, wherein the housing support structure, at least over an axial section which supports the bearing body in and counter to the delivery direction, has an axial thermal expansion which corresponds at least substantially to the axial thermal expansion of the bearing body over its axial section measured between the support locations.

19. The device according to claim 18, wherein the bearing body has in an axial section, per unit of axial length, an axial thermal expansion corresponding at least substantially to the axial thermal expansion of the container measured per unit of axial length.

20. The device according to claim 17, wherein the delivery means comprises a drive member and an output member that projects axially into the container in the delivery direction, these members being in engagement with one another in such a way that a drive movement of the drive member effects the output movement executed by the output member, and in that the support structure, at least over an axial section extending from the engagement between the drive member and the output member to a front end of the output member in the delivery direction, has an axial thermal expansion corresponding at least substantially to the axial thermal expansion of the output member measured between the engagement point and the front end of the output member.

21. The device according to claim 20, wherein, in an axial section extending from a bearing point of the drive member to the front end of the output member, the support structure has at least substantially the same thermal expansion as the delivery means, measured from the bearing point of the drive member to the front end of the output member.

22. The device according to claim 21, wherein the output member, from the engagement point to its front end, has, per unit of axial length, an axial thermal expansion corresponding at least substantially to the axial thermal expansion of the container measured per unit of axial length.

23. The device according to claim 22, wherein the axial thermal expansions compared to one another differ by at most about 500%.

24. The device according to claim 22, wherein the axial thermal expansions compared to one another differ by at most about 300%.

25. The device according to claim 1, further comprising a housing shell structure surrounding the housing support structure.

26. A device for administering a dose of a substance, the device comprising:
- a container for the substance, the container having an axial length and an axial coefficient of thermal expansion, the container being formed from glass;
- a delivery mechanism which acts on the substance, and
- a support structure comprising a first support shoulder disposed proximate a distal end of the support structure projecting substantially transversely with respect to a delivery direction which supports the container in the delivery direction and a second support shoulder disposed proximate a proximal end of the support structure projecting substantially transversely with respect to the delivery direction which supports the container counter to the delivery direction,
- wherein the support structure further comprises a distal opening sized and shaped to accommodate passage of the container into a receiving compartment of the support structure and a closure element configured to close the distal opening, wherein the closure element forms the first support shoulder and is non-destructively releasably coupled to the device, and
- wherein the support structure is formed as a sleeve-shaped body and has, over the axial length of the container, an axial coefficient of thermal expansion which, within a temperature range in which the device is used, differs by about 500% or less from the axial thermal expansion of the container.

27. The device according to claim 26, wherein the coefficient of thermal expansion of the support structure and the coefficient of thermal expansion of the container differ by at most 500%.

28. The device according to claim 26, wherein the support structure is formed from at least one of a metal and a metal alloy.

29. The device according to claim 26, wherein the support structure is configured such that a distal end of the container abuts the first support shoulder and a proximal end of the container abuts the second support shoulder.

* * * * *

UNITED STATES PATENT AND TRADEMARK OFFICE
CERTIFICATE OF CORRECTION

PATENT NO. : 8,343,099 B2
APPLICATION NO. : 11/388216
DATED : January 1, 2013
INVENTOR(S) : Daniel Peter et al.

It is certified that error appears in the above-identified patent and that said Letters Patent is hereby corrected as shown below:

In the Specification

Col. 5, Lines 19-20, "it is may be preferable" should read --it may be preferable--;

Col. 11, Line 21, "At one end, which way he referred to" should read --At one end, which may be referred to--; and Col. 12, Line 24, "outer thread 111" should read --outer thread 11--.

Signed and Sealed this
Twelfth Day of November, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,343,099 B2 | Page 1 of 1 |
| APPLICATION NO. | : 11/388216 | |
| DATED | : January 1, 2013 | |
| INVENTOR(S) | : Peter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1571 days.

Signed and Sealed this
Twenty-eighth Day of October, 2014

Michelle K. Lee
*Deputy Director of the United States Patent and Trademark Office*